US011287621B2

(12) United States Patent
Yamazaki et al.

(10) Patent No.: US 11,287,621 B2
(45) Date of Patent: Mar. 29, 2022

(54) BEAM GENERATION OPTICAL SYSTEM AND IMAGE CAPTURING APPARATUS PROVIDED WITH THE SAME

(71) Applicant: FUJITSU FRONTECH LIMITED, Tokyo (JP)

(72) Inventors: Kozo Yamazaki, Inagi (JP); Isao Iwaguchi, Inagi (JP)

(73) Assignee: FUJITSU FRONTECH LIMITED, Inagi (JP)

( * ) Notice: Subject to any disclaimer, the term of this patent is extended or adjusted under 35 U.S.C. 154(b) by 456 days.

(21) Appl. No.: 16/366,432

(22) Filed: Mar. 27, 2019

(65) Prior Publication Data

US 2019/0219803 A1      Jul. 18, 2019

Related U.S. Application Data

(63) Continuation of application No. PCT/JP2016/082052, filed on Oct. 28, 2016.

(51) Int. Cl.
*G02B 17/08* (2006.01)
*G02B 19/00* (2006.01)

(52) U.S. Cl.
CPC ....... *G02B 17/0868* (2013.01); *G02B 17/086* (2013.01); *G02B 19/0028* (2013.01); *G02B 19/0061* (2013.01)

(58) Field of Classification Search
CPC ............. G02B 17/061; G02B 17/0631; G02B 17/0652; G02B 17/0808; G02B 17/0824;
(Continued)

(56) References Cited

U.S. PATENT DOCUMENTS 2,683,394 A * 7/1954 Polanyi .............. G02B 17/0896
359/729
4,088,397 A * 5/1978 Jourdan ................. G02B 7/026
359/808
(Continued)

FOREIGN PATENT DOCUMENTS

JP      63058324 A    3/1988
JP      07168122 A    7/1995
(Continued)

OTHER PUBLICATIONS

Office action issued in corresponding Japanese patent application No. 2018-547026, dated Sep. 3, 2019 (with full machine translation).
(Continued)

*Primary Examiner* — Nicholas R. Pasko
(74) *Attorney, Agent, or Firm* — Greer Burns & Crain Ltd.

(57) ABSTRACT

An optical element includes: a first transmissive section 3 that causes light emitted from a light source to be incident on the optical element; a first reflection section 4 which is located at a facing section facing the first transmissive section and from which light incident from the first transmissive section is reflected; a second reflection section 5 which is located around the first transmissive section and from which the light reflected from the first reflection section is reflected; and a second transmissive section 6 that causes the light reflected from the second reflection section to be emitted out of the optical element in an optical axis direction of the light source.

6 Claims, 25 Drawing Sheets

(58) Field of Classification Search
CPC .............. G02B 17/084; G02B 17/0856; G02B 17/086; G02B 17/0864; G02B 17/0868; G02B 17/0872; G02B 19/0028; G02B 19/0047; G02B 19/0061

See application file for complete search history.

(56) References Cited

U.S. PATENT DOCUMENTS

| | | | | |
|---|---|---|---|---|
| 4,835,380 | A * | 5/1989 | Opheij | G02B 27/144 250/216 |
| 5,841,596 | A * | 11/1998 | Perlo | F21S 43/40 359/859 |
| 6,867,929 | B2 * | 3/2005 | Lopez-Hernandez | G02B 5/0278 250/503.1 |
| 6,896,381 | B2 * | 5/2005 | Benitez | G02B 19/0061 359/858 |
| 7,088,526 | B2 * | 8/2006 | Braun | G02B 17/004 359/627 |
| 7,181,378 | B2 * | 2/2007 | Benitez | G02B 19/0028 703/2 |
| 7,701,647 | B2 * | 4/2010 | Mitchell | G02B 17/0808 359/731 |
| 8,136,967 | B2 * | 3/2012 | Weaver | F21V 5/04 362/327 |
| 8,419,232 | B2 * | 4/2013 | Minano | F21S 41/322 362/328 |
| 9,329,374 | B2 * | 5/2016 | Otani | F21S 41/322 |
| 2003/0026002 | A1 | 2/2003 | Lopez-Hernandez et al. | |
| 2005/0213180 | A1 | 9/2005 | Lopez-Hernandez et al. | |
| 2013/0057971 | A1 * | 3/2013 | Zhao | G02B 13/06 359/731 |
| 2015/0140263 | A1 * | 5/2015 | Ohno | F21V 29/70 428/131 |

FOREIGN PATENT DOCUMENTS

| | | |
|---|---|---|
| JP | 2002341246 A | 11/2002 |
| JP | 2008036226 A | 2/2008 |
| JP | 2010060728 A | 3/2010 |

OTHER PUBLICATIONS

Written Opinion of the International Searching Authority of PCT/JP2016/082052, dated Dec. 20, 2016 (with partial English translation).

ISR issued in Int'l. App. No. PCT/JP2016/082052, dated Dec. 20, 2016.

Office action issued for CN 201680090116.6, dated Sep. 27, 2020 (with full machine translation).

* cited by examiner

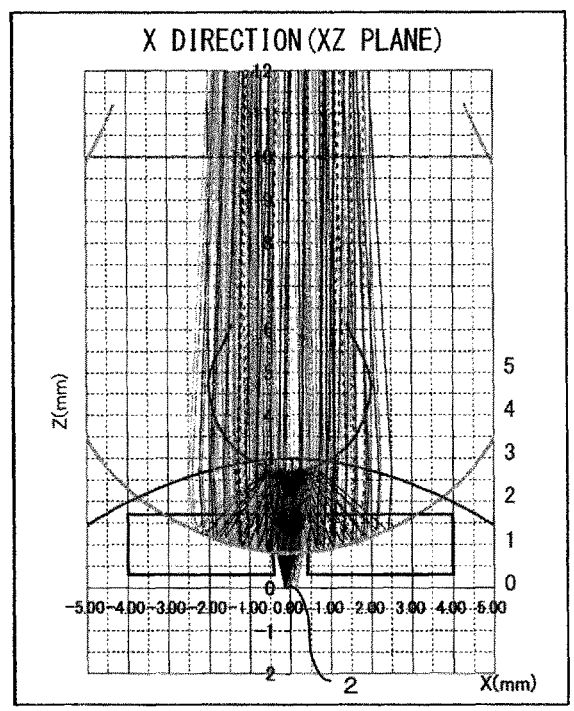
F I G. 4 A
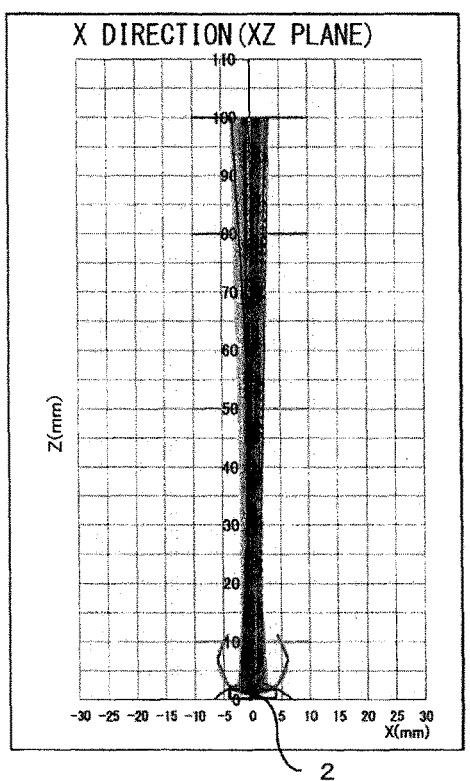
F I G. 4 B

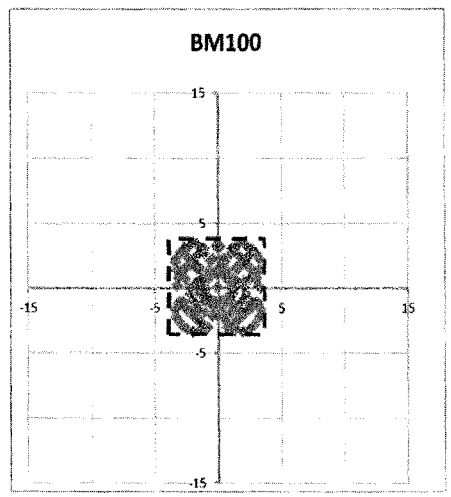
F I G. 4 C
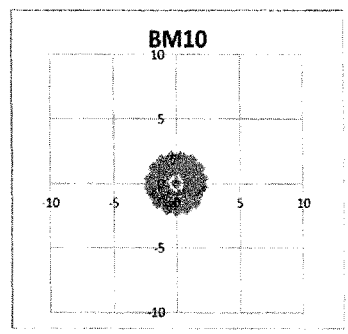
F I G. 4 D

| | |
|---|---|
| SIDE LENGTH RATIO | 8 8 % |
| AREA RATIO | 7 8 % |

F I G. 5

| EFFECTIVE AREA RATIO | REFLECTION LOSS | TRANSMISSIVE POWER RATIO | SPOT AREA RATIO | RADIANCE RATIO |
|---|---|---|---|---|
| 0.8976 | 0.81 | 0.7271 | 4 | 2.91 |

FIG. 6

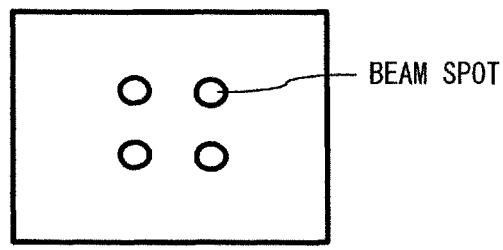
F I G. 1 4 A
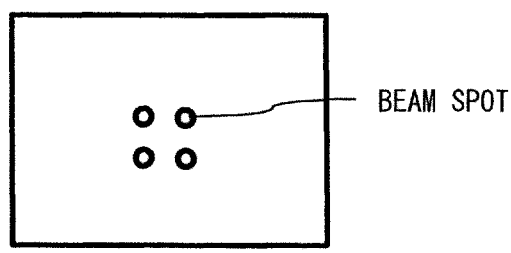
F I G. 1 4 B

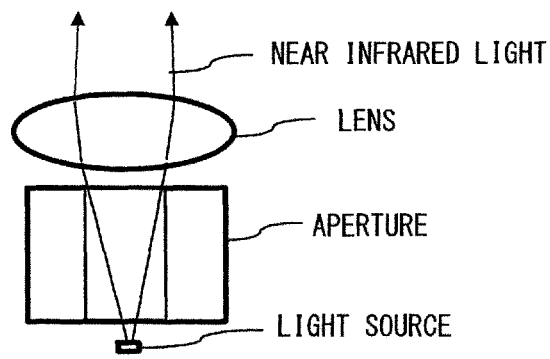
F I G. 17A
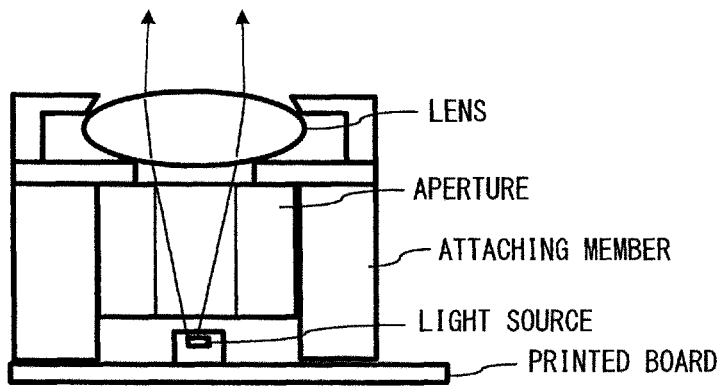
F I G. 17B
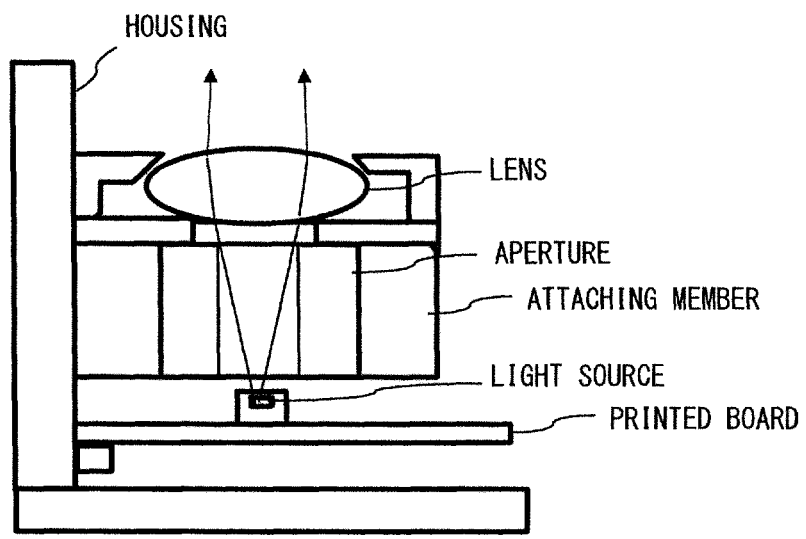
F I G. 17C

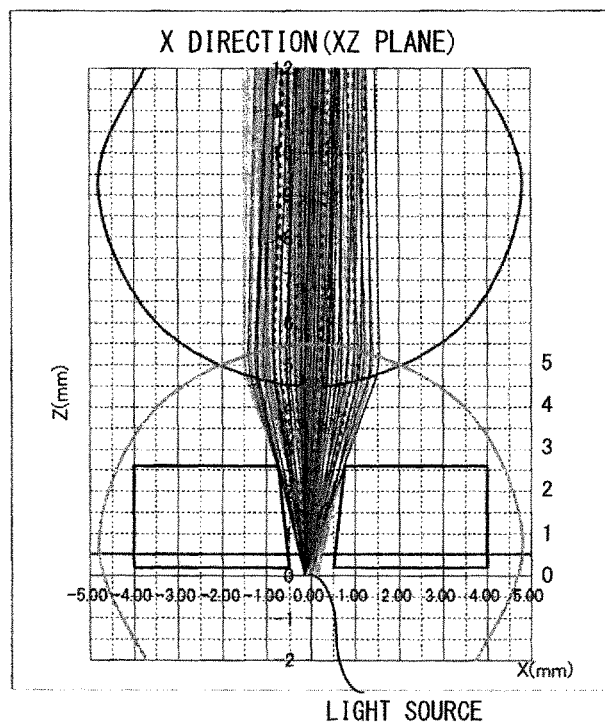
F I G. 18A
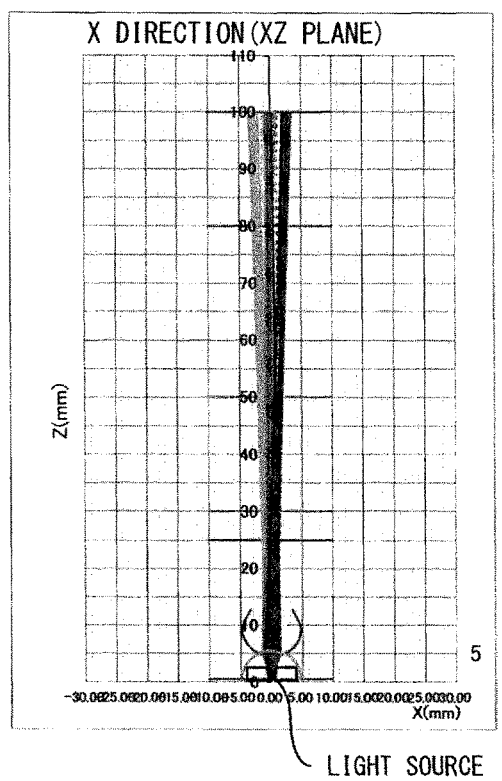
F I G. 18B

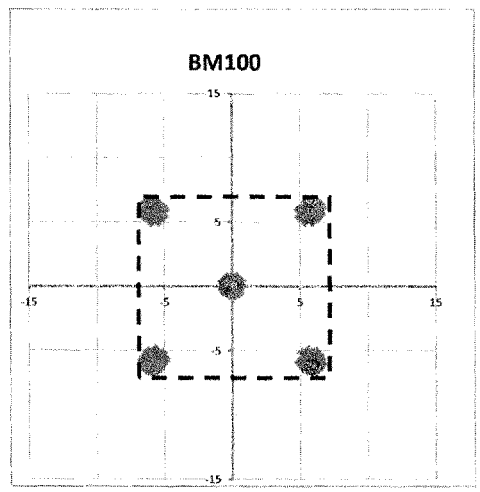
F I G. 19C
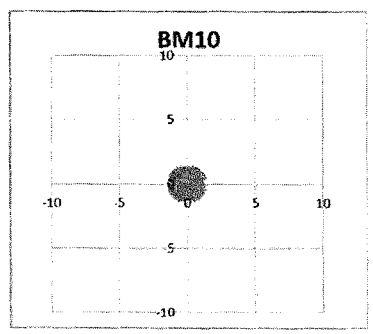
F I G. 19D

BEAM GENERATION OPTICAL SYSTEM AND IMAGE CAPTURING APPARATUS PROVIDED WITH THE SAME

CROSS-REFERENCE TO RELATED APPLICATIONS

This application is a continuation application of International PCT Application No. PCT/JP2016/082052 which was filed on Oct. 28, 2016.

BACKGROUND OF THE INVENTION

Field of the Invention

The present invention relates to a beam generation optical system for generating a light beam, the beam generation optical system emitting light from a light source via an optical element.

Description of the Related Art

As illustrated in FIG. 11, a palm-vein-image capturing apparatus irradiates a palm with ranging beams (also referred to as light beams) emitted from ranging LED light sources disposed at four corners (see FIGS. 12 and 13) and captures images of beam spots (four spots with reference to this example) depicted in FIG. 15 resulting from the irradiation of the palm, thereby measuring a distance. FIG. 12 illustrates the appearance of a conventional image capturing apparatus. FIG. 13 illustrates a plane view of illumination LED light sources and ranging LED light sources depicted in FIG. 12. FIGS. 14A and 14B illustrate images indicating beam spots captured by an image sensor.

The beam spots depicted in FIG. 14A are larger than those depicted in FIG. 14B. This is because the image in FIG. 14A is an image indicating beam spots captured when a subject such as a palm is close to an image capturing apparatus, while the image in FIG. 14B is an image indicating beam spots captured when the subject is distant from the image capturing apparatus. The height of each beam spot on the subject and therefore an inclination of the subject can be determined by measuring the distance between the center point and each of the beam spots on the captured image.

An infrared LED, not a laser, is used as a light source in view of the demand of small size and low cost. Unlike a laser, an LED light source (also simply referred to as a light source) has a chip surface that emits light, and hence the size of the light source is limited. Accordingly, a beam spot for ranging that is seen on a subject is essentially a spot provided by projecting the shape of a light source chip, as depicted in FIG. 16.

FIGS. 17A-17C illustrate an example of a conventional ranging-beam generation optical system (also referred to as a ranging optical system or a beam generation optical system) to be mounted on an image capturing apparatus. Near infrared light from a light source passes through an aperture and is then emitted upward by a lens (spherical lens). FIG. 17A depicts a basic configuration for a ranging-beam generation optical system. To mount the ranging-beam generation optical system on a palm-vein-image capturing apparatus, an attaching member for the optical system may be, as depicted in FIG. 17B, provided with an aperture and a lens and attached to a printed board, or may be, as depicted in FIG. 17C, integrated with each of the four corners of a housing without being in contact with the printed board.

FIGS. 18A and 18B illustrate examples of movements of light lays (beam) of a beam generation optical system. More particularly, FIGS. 18A and 18B each depict light rays on an XY plane, where the XY plane is a plane on which a light source is placed, and Z direction is a direction from the light source toward a subject. This is also applicable to FIGS. 19A and 19B, which will be described hereinafter, and to FIGS. 2A, 2B, 4A, and 4B, which will be described with reference to embodiments.

In FIGS. 18A and 18B, a lens is distant from the light source by 5 mm, and a beam is emitted upward from the lens. FIG. 18C depicts a beam spot distant from the light source by 100 mm, while FIG. 18D depicts a beam spot distant from the light source by 10 mm. These beam spots are provided by projecting a square LED chip using the lens.

Palm-vein-image capturing apparatuses are used in various fields, including automated teller machines (ATMs) and entrance and exit management apparatuses. In recent years, thin palm-vein-image capturing apparatuses have been incorporated into note PCs and tablet PCs (see, for example, Japanese Laid-open Patent Publication No. 2008-36226). In accordance with the trend of making note PCs and tablet PCs lighter and thinner, palm-vein-image capturing apparatuses have been required to be thin. In order to achieve a thin palm-vein-image capturing apparatus, it is important to make thinner a ranging-beam generation optical system such as that depicted in FIGS. 17A-17C, in addition to providing a thin imaging system that includes an imaging lens and an image sensor.

In the example depicted in FIG. 18C, a beam spot with an area of about 7 mm×7 mm is obtained on a screen distant from the light source by 100 mm. In this example, the distance from the light source to the lens is 5 mm. By contrast, FIGS. 19A-19D depict characteristics achieved when the beam generation optical system is made thinner by setting 2.5 mm as the distance from the light source to the lens (i.e., ½ of the length in the example of FIG. 18A). A beam spot with an area of about 14 mm×14 mm (see FIG. 19C) is obtained on a screen distant from the light source by 100 mm, and a beam spot smaller than this cannot be obtained. Here, the solid angle of the light rays which enters a lens to be utilized to form a ranging beam are the same between FIGS. 18A and 19A.

FIGS. 20A and 20B illustrate relationships between beam spot size and a distance between a light source and a lens. As described above, a beam spot is actually obtained by projecting light from a light source by using a lens. FIG. 20A depicts a situation in which an image of an LED chip with edges each having a length of a is enlarged at a ratio of H/h and projected onto an object as a square with sides each having a length of A, where h indicates a distance between the light source and the lens, and H indicates a distance between the lens and the object.

However, when h/2 is set as the distance between the light source and the lens as depicted in FIG. 20B in order to make the optical system thinner, the ratio to the distance H to the object, or the magnification of the image, is doubled, and hence the image projected onto the object is a square with sides each having a length of 2×A.

Doubling each side of a beam spot quadruplicates a beam spot area, and hence the radiance is reduced to one-fourth when the amount of emitted light (power) remains the same. This means that the output is reduced to one-fourth because a beam spot image obtained by the image sensor in the imaging system has a proportional relationship with the radiance. Meanwhile, as the distance becomes longer, the beam spot size is increased. This causes a problem of a decreased degree of separation between four beam spots on the palm. After all, making the optical system thinner will decrease the sensitivity and accuracy of the ranging function. Accordingly, the conventional beam generation optical system has a trade-off between making the system thinner and characteristics of ranging beams and can be made thinner only to a limited degree.

To achieve a small beam spot, the lens and the light source need to have a long distance therebetween to maintain a low projection magnification, as depicted in FIG. 20A. However, providing a long distance between the lens and the light source hinders the providing of a thin image capturing apparatus, as described above.

SUMMARY OF THE INVENTION

The present invention is directed to a beam generation optical system that causes light emitted from a light source to be incident on an optical element and causes the incident light to be reflected and emitted out of the optical element so as to generate a light beam, the optical element including: a first transmissive section that causes the light emitted from the light source to be incident on the optical element; a first reflection section which is located at a facing section facing the first transmissive section and from which light incident from the first transmissive section is reflected; a second reflection section which is located around the first transmissive section and from which the light reflected from the first reflection section is reflected; and a second transmissive section that causes the light reflected from the second reflection section to be emitted out of the optical element in an optical axis direction of the light source.

BRIEF DESCRIPTION OF THE DRAWINGS

FIG. 4A illustrates an example of a movement of light rays of a beam generation optical system that includes an optical element in accordance with a second embodiment;

FIG. 4B illustrates an example of a movement of light rays of a beam generation optical system that includes an optical element in accordance with a second embodiment;

FIG. 4C illustrates a beam spot on a screen distant from a light source of a beam generation optical system by 100 mm, the beam generation optical system including an optical element in accordance with a second embodiment;

FIG. 4D illustrates a beam spot on a screen distant from a light source of a beam generation optical system by 10 mm, the beam generation optical system including an optical element in accordance with a second embodiment;

FIG. 5 illustrates that a second embodiment provides a beam spot size that is smaller than that provided by a first embodiment;

FIG. 6 illustrates advantageous effects of a second embodiment;

FIG. 14A illustrates an exemplary image indicating beam spots that is captured by a conventional image capturing apparatus;

FIG. 14B illustrates an exemplary image indicating beam spots that is captured by a conventional image capturing apparatus;

FIG. 17A illustrates an example of the basic configuration of a conventional beam generation optical system;

FIG. 17B illustrates an example of the mounting of a conventional beam generation optical system;

FIG. 17C illustrates an example of the mounting of a conventional beam generation optical system;

FIG. 18A illustrates an example of a movement of a light lay of a conventional beam generation optical system;

FIG. 18B illustrates an example of a movement of a light lay of a conventional beam generation optical system;

FIG. 19C illustrates beam spots provided on a screen by a conventional beam generation optical system when the distance to the lens is ½ of the distance indicated in FIG. 18C, the screen being distant from a light source by 100 mm;

FIG. 19D illustrates a beam spot provided on a screen by a conventional beam generation optical system when the distance to the lens is ½ of the distance indicated in FIG. 18C, the screen being distant from a light source by 10 mm;

DETAILED DESCRIPTION OF THE PREFERRED EMBODIMENTS

First Embodiment

The following describes a first embodiment by referring to drawings. The present invention features optical elements, and non-optical-element components of an image capturing apparatus of the invention that includes a beam generation optical system are similar to those seen in the prior art. Accordingly, descriptions of such non-optical-element components are omitted herein. This is also applicable to the other embodiments described hereinafter. The image capturing apparatus of the present invention, i.e., an image capturing apparatus that includes a beam generation optical system, does not need to be provided with an aperture, i.e., a component of the conventional image capturing apparatus.

Figure 1A:
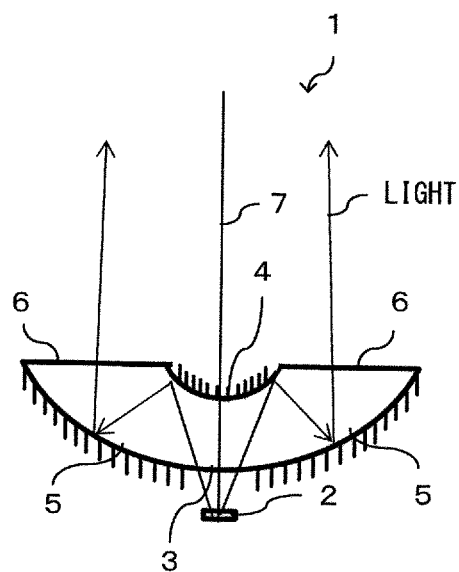
FIG. 1A is a side view of an optical element in accordance with a first embodiment as seen from the side.
Figure 1B:
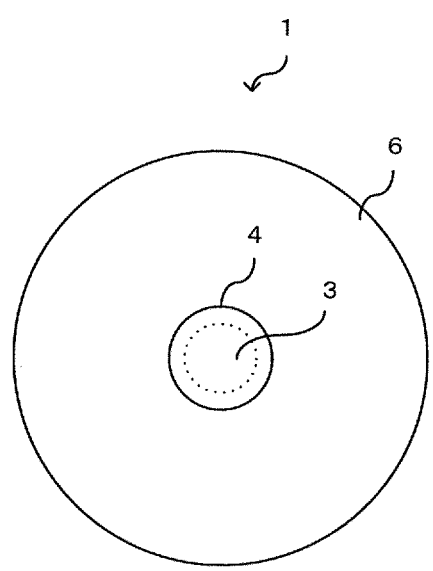
FIG. 1B is a plane view of an optical element in accordance with a first embodiment as seen from above.

FIGS. 1A and 1B each depict the appearance of an optical element in accordance with the first embodiment. FIG. 1A is a side view of an optical element 1 as seen from the side. FIG. 1B is a plane view of the optical element 1 as seen from above. As with the conventional spherical lens, the optical element 1 depicted in FIGS. 1A and 1B receives light emitted from a light source (LED) 2.

The optical element 1 includes, at a center of a light-incidence side (light-source-2 side), a transmissive section (first transmissive section) 3 through which light emitted from a light source 2 enters the optical element 1. The optical element 1 also includes, at a center of a light-emission side (an opposite side from the side on which the light source 2 is disposed), a reflection section (first reflection section) 4 from which light incident through the transmissive section 3 is reflected. The transmissive section 3 and the reflection section 4 face each other. The transmissive section 3 and the reflection section 4 as seen from above have circular shapes as depicted in FIG. 1B, but the shapes are not limited to this.

The optical element 1 also includes, around (at a portion surrounding) the transmissive section 3, a reflection section (second reflection section) 5 from which light reflected from the reflection section 4 is reflected. The reflection section 5 forms a convex shape on the light-source-2 side. The optical element 1 also includes, around (at a portion surrounding) the first reflection section 4, a transmissive section (second transmissive section) 6 through which light reflected from the reflection section 5 is emitted out of the optical element 1 along an optical axis 7 toward a subject (e.g., a palm) (not illustrated). The reflection section 5 and the transmissive section 6 face each other.

As described above, the optical element 1 is a lens that forms a convex shape toward the light source 2 (downward convex shape), as depicted in FIG. 1A. The lens of the optical element 1 may be glass or may be another material, e.g., plastic. This is also applicable to the materials for the optical elements in the other embodiments described hereinafter. The transmissive section 3 and the reflection section 4 each form a convex shape toward the light source 2 but may each form a planar shape (flat surface).

Light emitted from the light source 2 enters the optical element 1 through the transmissive section 3 of the optical element 1. While the region through which light enters (transmissive section 3) is a lens surface, a reflective film is formed on the outer surface of the optical element 1 so as to cover the reflection section 5 located around (at a portion surrounding) the transmissive section 3 (e.g., formed through meatal deposition such as aluminum deposition). Similarly, a reflective film is formed on the outer surface of the optical element 1 so as to cover the reflection section 4. As a result, as in the case of the aperture of the conventional ranging-beam generation optical system (beam generation optical system), only light rays among the light rays emitted from the light source 2 that forma predetermined angle with the optical axis 7 are used to generate a beam, while the other light rays are blocked by the refractive film of the reflection section 5. The light that has entered the optical element 1 through the transmissive section 3 is incident on the reflection section 4 provided over the transmissive section 3.

As described above, a reflective film is formed on the outer surface of the optical element 1 so as to cover the reflection section 4, and the reflection section 4 serves (functions) as a convex mirror for incident light. Accordingly, the reflection section 4 reflects incident light toward the light incidence surface (toward the light source 2) while enlarging the light. The light that returns to the incidence-surface side after being reflected is also reflected upward from the reflective film formed on the outer surface of the optical element 1 so as to cover the reflection section 5 and is then emitted through the transmissive section 6 that faces the reflection section 5. The reflection section 5, which serves as a concave mirror, emits light while converging the light.

Figure 18C:
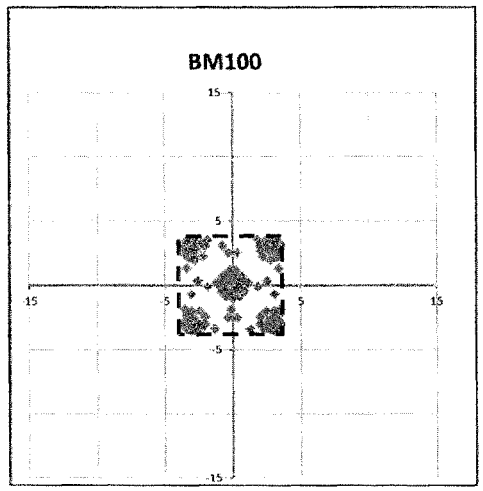
FIG. 18C illustrates beam spots provided on a screen by a conventional beam generation optical system, the screen being distant from a light source by 100 mm.
Figure 18D:
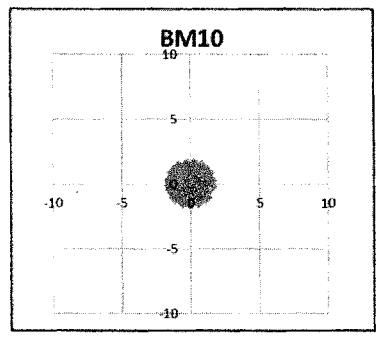
FIG. 18D illustrates a beam spot provided on a screen by a conventional beam generation optical system, the screen being distant from a light source by 10 mm.

Light turns around upward and downward within the optical element 1, as described above, and thus follows an extended light path, and the light is then emitted toward a subject while maintaining a low projection magnification effectively. As a result, a beam spot on a screen distant from the light source 2 by 100 mm has, as depicted in FIG. 2C, a size of about 7.6 mm×7.6 mm, which is almost equal to the size indicated in FIG. 18C. Meanwhile, FIG. 2D illustrates the size of a beam spot on a screen distant from the light source 2 by 10 mm.

Figure 2A:
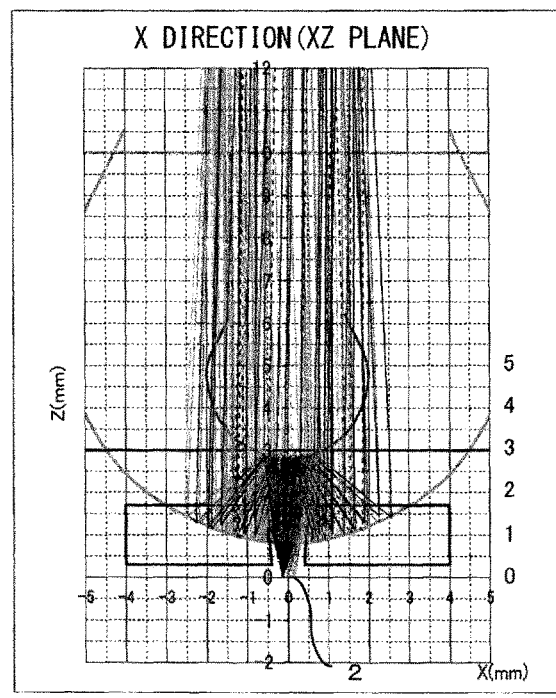
FIG. 2A illustrates an example of a movement of light rays of a beam generation optical system that includes an optical element in accordance with a first embodiment.
Figure 2B:
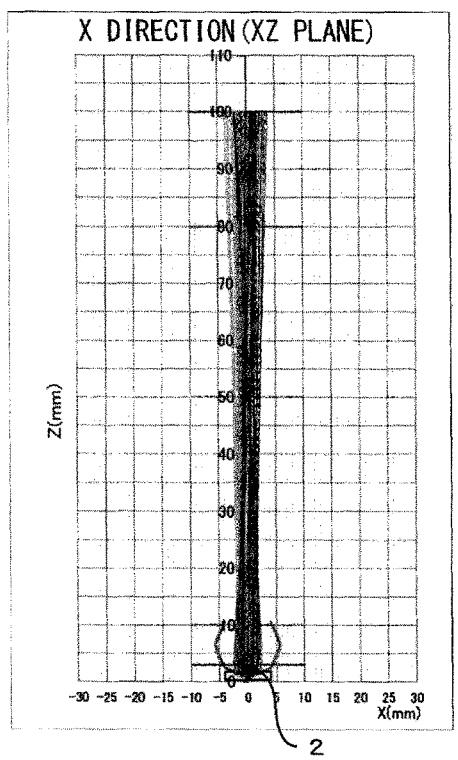
FIG. 2B illustrates an example of a movement of light rays of a beam generation optical system that includes an optical element in accordance with a first embodiment.
Figure 2C:
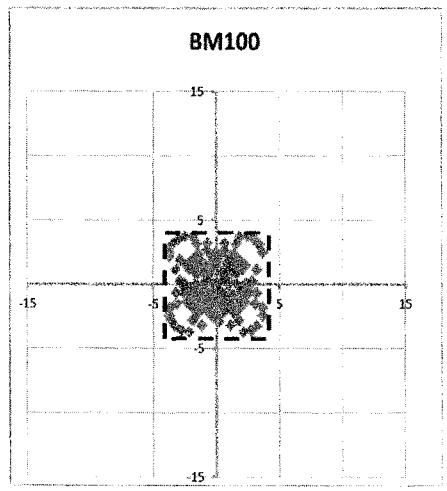
FIG. 2C illustrates a beam spot on a screen distant from a light source of a beam generation optical system by 100 mm, the beam generation optical system including an optical element in accordance with a first embodiment.
Figure 2D:
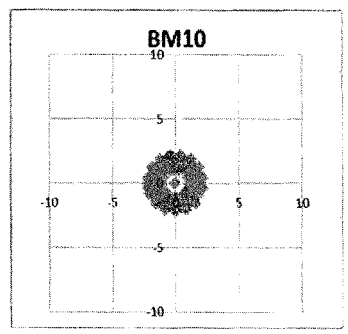
FIG. 2D illustrates a beam spot on a screen distant from a light source of a beam generation optical system by 10 mm, the beam generation optical system including an optical element in accordance with a first embodiment.
Figure 19A:
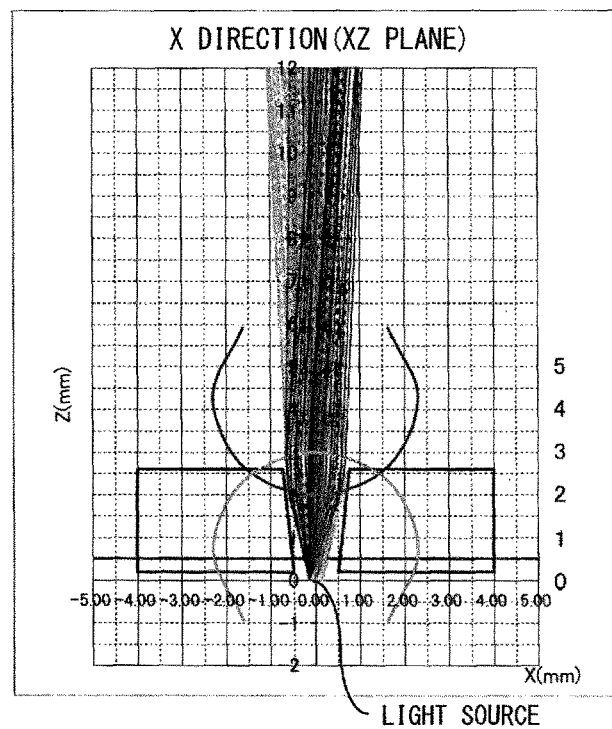
FIG. 19A illustrates an example of a movement of light rays provided by a conventional beam generation optical system when the distance to the lens is ½ of the distance indicated in FIG. 18C.
Figure 19B:
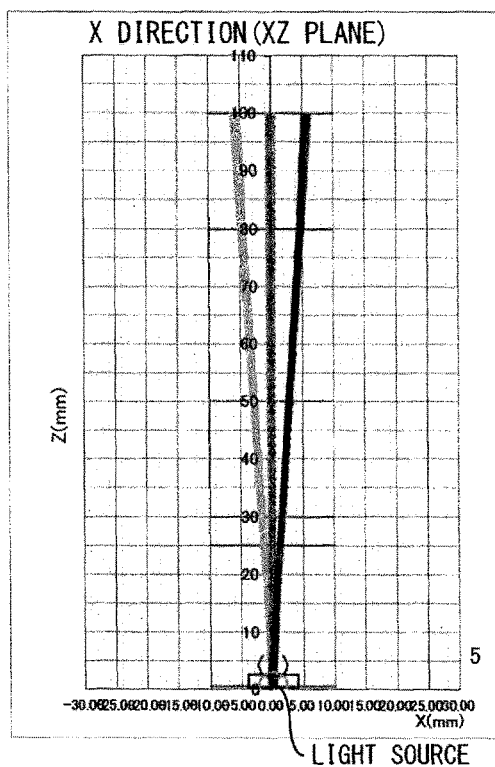
FIG. 19B illustrates an example of a movement of light rays provide by a conventional beam generation optical system when the distance to the lens is ½ of the distance indicated in FIG. 18C.
Figure 20A:
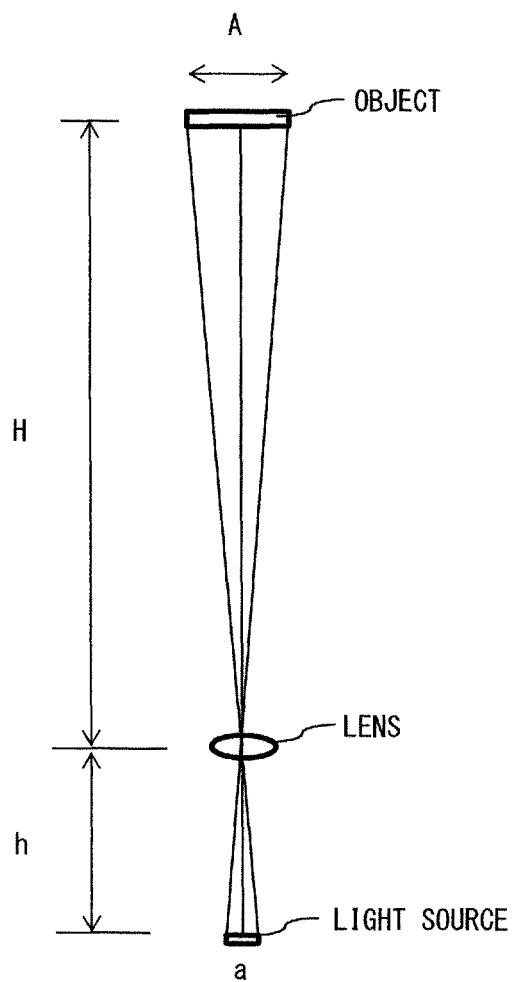
FIG. 20A illustrates, for a conventional beam generation optical system, a relationship between beam spot size and a distance h between a light source and a lens.
Figure 20B:
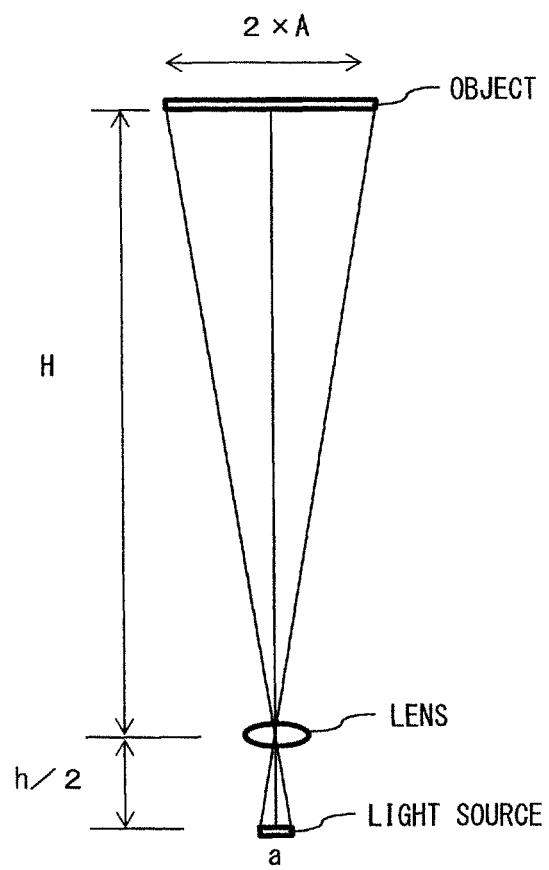
FIG. 20B illustrates, for a conventional beam generation optical system, a relationship between beam spot size and a distance h/2 between a light source and a lens.

The beam generation optical system of the first embodiment includes, as depicted in FIGS. 2A and 2B, an emission surface at a position distant from the light source 2 by 3 mm, which is the same as the position of the lens emission-surface that is depicted in FIG. 19A. Accordingly, the beam spot size is almost the same as that of a beam spot provided by the ranging-beam generation optical system depicted in FIG. 18A, while the height is about ½ of that of the ranging-beam generation optical system depicted in FIG. 18A, i.e., the configuration is thinner. This means that the configuration can be made thinner while the radiance of a spot for which spot image outputs are to be determined remains the same.

Second Embodiment

Figure 3A:
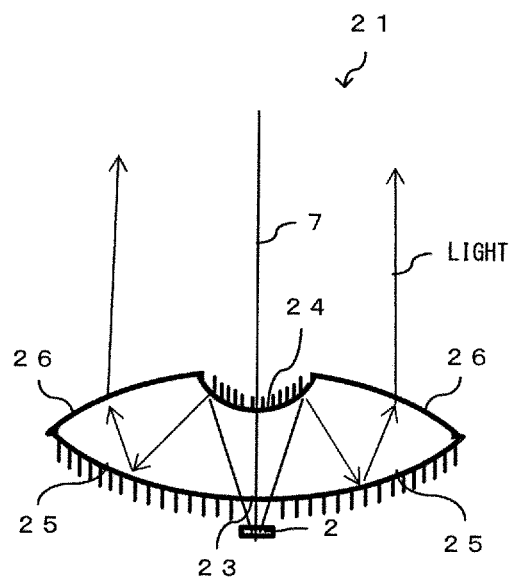
FIG. 3A is a side view of an optical element in accordance with a second embodiment as seen from the side.
Figure 3B:
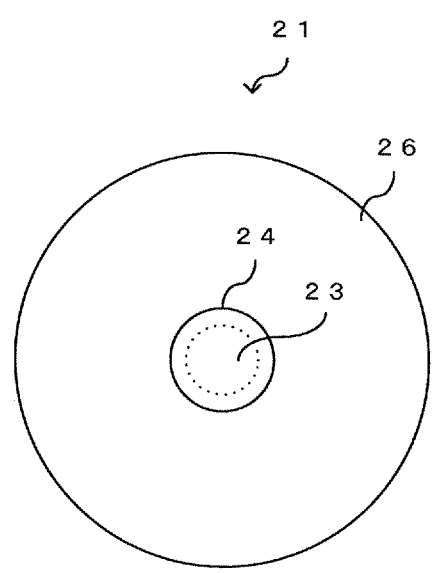
FIG. 3B is a plane view of an optical element in accordance with a second embodiment as seen from above.

The following describes a second embodiment by referring to drawings. FIGS. 3A and 3B each depict the appearance of an optical element in accordance with the second embodiment. FIG. 3A is a side view of an optical element 21 as seen from the side. FIG. 3B is a plane view of the optical element 21 as seen from above. As with the optical element 1 in accordance with the first embodiment, the optical element 21 depicted in FIGS. 3A and 3B receives light emitted from a light source (LED) 2.

While the optical element 1 of the first embodiment includes a base having a downward convex shape, the optical element 21 of the second embodiment includes a base having convex shapes on both sides, as depicted in FIG. 3A. In particular, a second reflection section 25 forms a convex shape on the light-source-2 side, and a second transmissive section 26 forms a convex shape on an opposite side from the light-source-2 side.

The optical element 21 includes, at a center of a light-incidence side (light-source-2 side), a transmissive section (first transmissive section) 23 through which light emitted from the light source 2 enters the optical element 21. The optical element 21 also includes, at a center of a light-emission side (an opposite side from the side on which the light source 2 is disposed), a reflection section (first reflection section) 24 from which light incident through the transmissive section 23 is reflected. The transmissive section 23 and the reflection section 24 face each other. The transmissive section 23 and the reflection section 24 as seen from above have circular shapes as depicted in FIG. 3B, but the shapes are not limited to this. The transmissive section 23 and the reflection section 24 each form a convex shape toward the light source 2 but may each forma planar shape (flat surface). This is also applicable to a third embodiment described hereinafter.

The optical element 21 also includes, around (at a portion surrounding) the transmissive section 23, a reflection section (second reflection section) 25 from which light reflected from the reflection section 24 is reflected. The reflection section 25 forms a convex shape on the light-source-2 side. This is also applicable to the third embodiment described hereinafter. The optical element 21 also includes, around (at a portion surrounding) the first reflection section 24, a transmissive section (second transmissive section) 26 through which light reflected from the reflection section 25 is emitted out of the optical element 21 along an optical axis 7 toward a subject (e.g., a palm) (not illustrated). The reflection section 25 and the transmissive section 26 face each other.

As in the first embodiment, a reflective film is formed on the outer surface of the optical element 21 so as to cover the reflection section 24 (e.g., formed through meatal deposition such as aluminum deposition). A reflective film is also formed on the outer surface of the optical element 21 so as to cover the reflection section 25. The reflective surface of the reflective film may be a metal-deposited surface or may be a refractive surface formed by a multilayer film.

FIGS. 4A-4D depict examples of results of light-ray simulations for a beam generation optical system using the optical element 21 (reflecting optical system) of the second embodiment. While the optical element 1 of the first embodiment includes, as a base, a lens having a downward convex shape (a planer shape and a convex shape on the upper side), the optical element 21 of the second embodiment includes a lens having convex shapes on both sides. Accordingly, the curvature of the emission surface is included in design parameters of the optical element 21, thereby achieving a high design freedom. As a result, a beam spot size at a position distant from the light source 2 by 100 mm is 6.7 mm×6.7 mm, as depicted in FIG. 4C. Meanwhile, FIG. 4D indicates the size of a beam spot on a screen distant from the light source 2 by 10 mm. As in the first embodiment, the beam generation optical system of the second embodiment has, as depicted in FIGS. 4A and 4B, an emission surface located at position distant from the light source 2 by mm, which is the same as the position of the lens emission-surface depicted in FIG. 19A.

Figure 5:
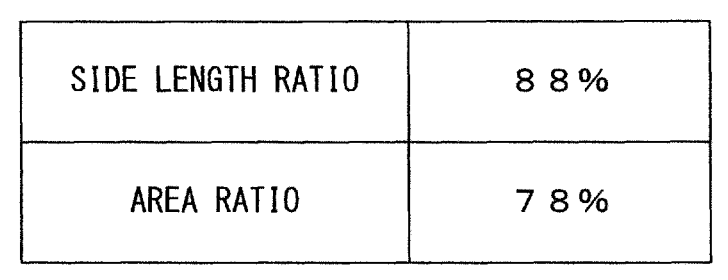

The side length of the beam spot in accordance with the second embodiment is 6.7 mm, although the side length of the beam spot in accordance with the first embodiment is 7.6 mm. As indicated in FIG. 5, the ratio of a side length is 88% and therefore the ratio of the beam spot area is 78% between the second embodiment and the first embodiment. Accordingly, the second embodiment has the advantageous effect of achieving a smaller beam spot.

The following quantitively describes the advantageous effect of the second embodiment by comparing the second embodiment with the prior art depicted in FIG. 19A. In addition to the conventional path of light emitted from the light source 2 into and then out of the lens, the configuration of the second embodiment includes the feature wherein light is reflected from the center on the emission side (first reflection section 24) and also reflected from the reflective surface at the surrounding portion on the incidence side (second reflection section 25), i.e., the light is reflected twice (this is also applicable to the other embodiments). When light is eventually emitted from the emission surface, the center of the emission side (first reflection section 24) does not allow passage of light rays, i.e., functions as an ineffective region.

Accordingly, in comparison with the prior art, the second embodiment is accompanied by a power loss that corresponds to the product of an effective area ratio and a reflection loss. On the other hand, the second embodiment has the advantageous effect of achieving a small beam spot area, i.e., achieving a high radiance (illumination intensity). As depicted in FIG. 6, while the second embodiment provides a transmissive power ratio of 0.7271 that is the product of the effective area ratio and the reflection loss, i.e., a lower value than in the prior art, the second embodiment reduces the beam spot area to ¼ and thus achieves a power density of 4, thereby providing a radiance ratio (an essential advantageous effect) of 2.91, i.e., the product of the transmissive power ratio and the power density. Hence, a high radiance ratio is provided even when the transmissive power ratio is low, so that a thin image capturing apparatus can be achieved without decreasing the sensitivity and accuracy of the ranging function.

Figure 7:
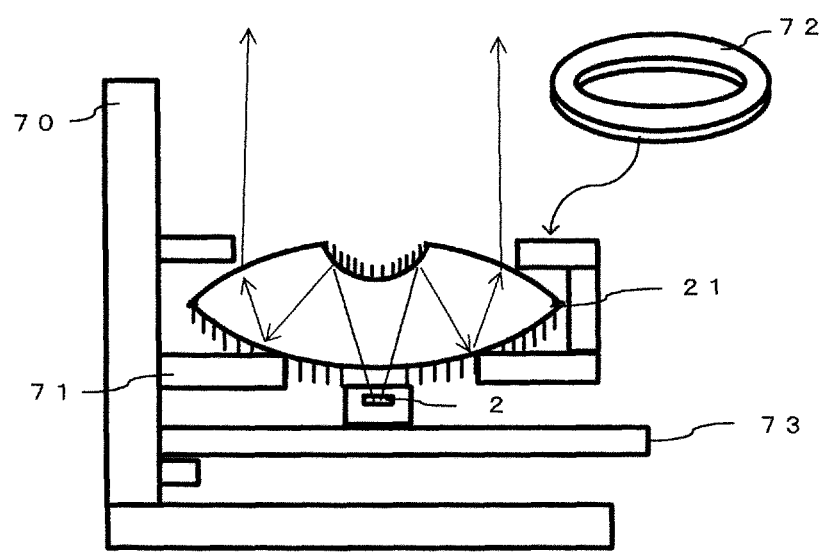
FIG. 7 illustrates an example of the mounting of an optical system in accordance with a second embodiment.

FIG. 7 illustrates an example of the mounting of the optical element 21 in accordance with the second embodiment. An attaching part 71 for an optical element 21 (ranging optical system) is integrated with each of four corners of a housing 70 of the image capturing apparatus, and the optical element 21 is mounted onto the attaching part 71. A cap 72 is fitted over and thus fixes the optical element 21. A printed board 73 provided with the light source 2 can be attached to the housing 70 without being in contact with the attaching part 71. As long as passage of a light beam traveling along an optical axis through the second transmissive section 26 is not hindered, the cap 72 can have any size. In this example, the cap 72 has a circular shape. However, as long as the optical element 21 can be fixed and passage of a light beam is not hindered, the shape of the cap 72 is not limited to a circular shape. Note that optical elements in accordance with other embodiments can be mounted in the same manner.

Third Embodiment

The following describes a third embodiment by referring to drawings. In the embodiments described above, the optical element includes a base having a downward convex shape (a planer shape and a convex shape on the upper side) or a base having convex shapes on both sides, and metal is deposited on portions of the optical element so that these portions can function as reflective surfaces. In the third embodiment and a fourth embodiment described hereinafter, optical elements different from those described above are used in consideration of manufacturability and costs.

Figure 8A:
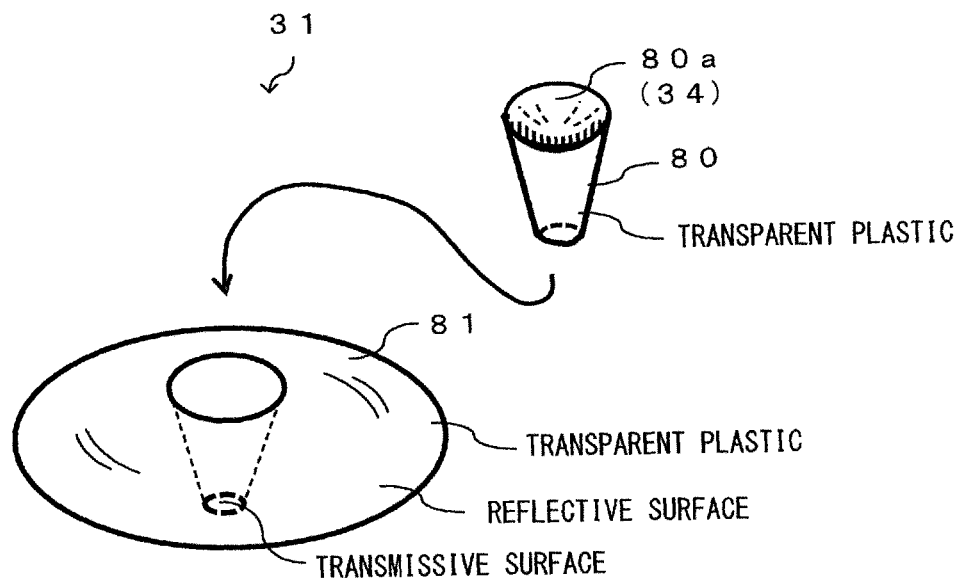
FIG. 8A is a perspective view of an optical element in accordance with a third embodiment as seen obliquely from above.
Figure 8B:
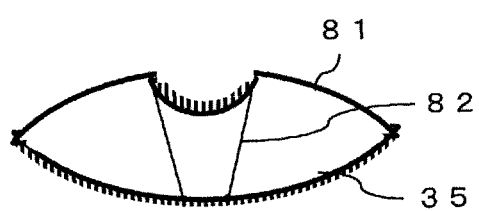
FIG. 8B is a side view of an optical element in accordance with a third embodiment as seen from the side.

FIGS. 8A and 8B each depict the appearance of an optical element in accordance with the third embodiment. FIG. 8A is a perspective view of an optical element 31 as seen obliquely from above. FIG. 8B is a side view of the optical element 31 as seen from the side. As with the optical element 21 in accordance with the second embodiment, the optical element 31 depicted in FIGS. 8A and 8B receives light emitted from a light source 2.

The optical element 31 of the third embodiment has a shape similar to that of the optical element 21 of the second embodiment. In the third embodiment, however, the optical element 31 includes a plurality of members (two members with reference to this embodiment); these members are assembled to function as the optical element 31. In particular, the optical element 31 includes: a member 80 that forms a convex mirror at a center of the optical element 31; and a member 81 that includes a void at a center thereof into which the member 80 is incorporated. The member 80 has functions of the first transmissive section 23 and the first reflection section 24 of the optical element 21 of the second embodiment. The member 81 has functions of the second reflection section 25 and the second transmissive section 26 of the optical element 21 of the second embodiment.

In the third embodiment, an upper section 80a (first reflection section 34) of the member 80 undergoes metal deposition, and a second reflection section 35 of the member also undergoes metal deposition. In combining the metal-deposited members, an adhesive, e.g., a lens bond, is applied to an interface 82 between the members 80 and 81. Thus, the members are bonded together to form the optical element 31. The adhesive applied to the interface 82 has a refractive index equal to that of the members 80 and 81.

The members 80 and 81 are, for example, transparent plastic. However, the material for the members 80 and 81 is not limit to this.

Fourth Embodiment

Figure 9A:
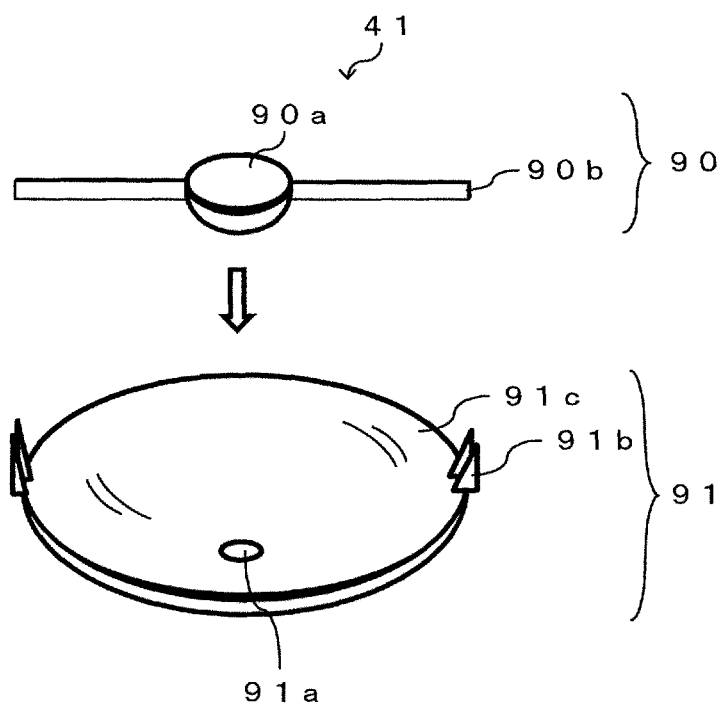
FIG. 9A is a perspective view of an optical element in accordance with a fourth embodiment as seen obliquely from above.
Figure 9B:
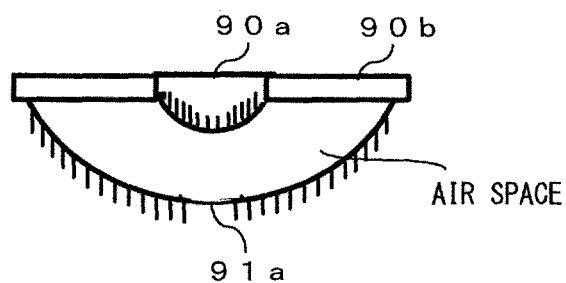
FIG. 9B is a side view of an optical element in accordance with a fourth embodiment as seen from the side.

The following describes a fourth embodiment by referring to drawings. FIGS. 9A and 9B each depict the appearance of an optical element in accordance with the fourth embodiment. FIG. 9A is a perspective view of an optical element 41 as seen obliquely from above. FIG. 9B is a side view of the optical element 41 as seen from the side. As with the optical element 1 in accordance with the first embodiment, the optical element 41 depicted in FIGS. 9A and 9B receives light emitted from a light source 2.

The optical element 41 of the fourth embodiment includes, as in the third embodiment, a plurality of members (members 90 and 91) but is not a lens base. The member 90 has functions of the first reflection section 4 of the optical element 1 of the first embodiment. The member 91 has functions of the first transmissive section 3 and the second reflection section 5 of the optical element 1 of the first embodiment. In the fourth embodiment, the optical element 41 does not include the second transmissive section 6 described above with reference to the first embodiment but includes an air space.

The member 90 includes a convex reflective mirror (convex mirror) 90a and an attachment rib 90b. The convex reflective mirror 90a has formed thereon the reflective film of the other embodiments described above. Accordingly, when the members 90 and 91 have been combined, light incident through a light incidence section 91a of the member 91 can be reflected while being expanded. The convex reflective mirror 90a may correspond to the first reflection section 4 of the first embodiment. The attachment rib 90b, which is used to attach the member 90 to the member 91, is attached to support parts 91b of the member 91 so as to form the optical element 41.

The member 91 includes the light incidence section 91a through which light from the light source 2 incident, the support parts 91b for supporting the member 90, and a concave reflective mirror (concave mirror) 91c. As with the first transmissive section 3 of the optical element 1 of the first embodiment, the light incidence section 91a is located at a center of the concave reflective mirror (concave mirror) 91c. The support parts 91b are configured to support the member 90 by sandwiching the attachment rib 90b, but the configuration of the support parts 91b is not limited to this. The concave reflective mirror 91c has formed thereon the reflective film of the other embodiments described above. Thus, light reflected from the convex reflective mirror 90a can be reflected along an optical axis toward a subject (not illustrated). The concave reflective mirror 91c may correspond to the second reflection section 5 of the first embodiment.

Such a configuration allows the power loss to be limited to a low level since the inside of the optical element 41 is an air space.

Figure 10A:
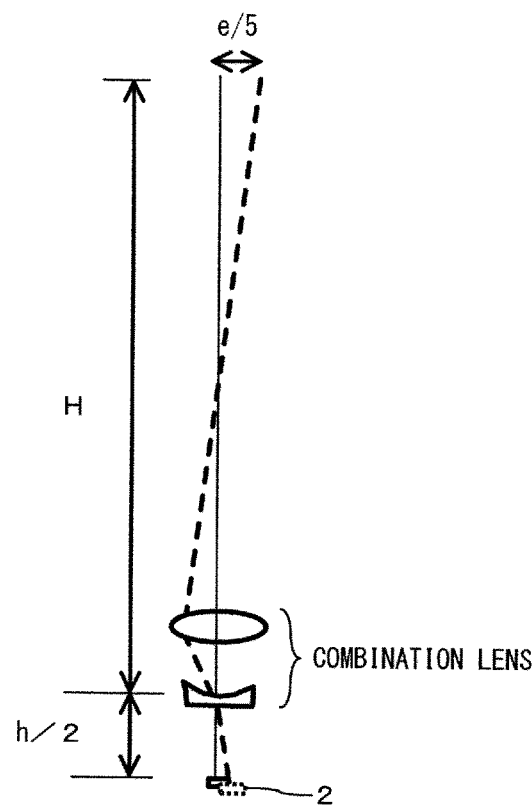
FIG. 10A illustrates other advantageous effects of the invention.
Figure 10B:
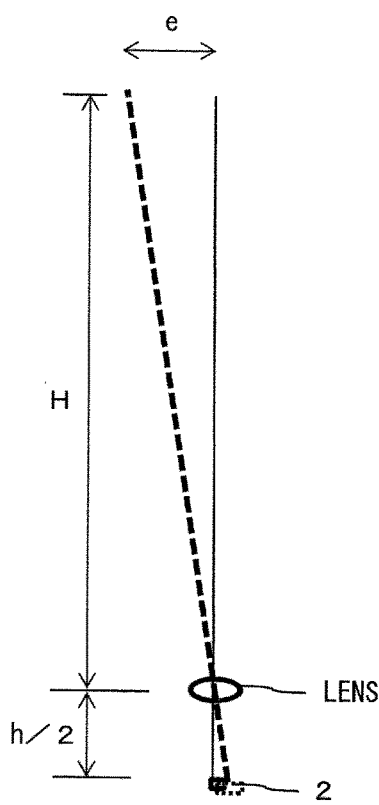
FIG. 10B illustrates other advantageous effects of the invention.
Figure 11:
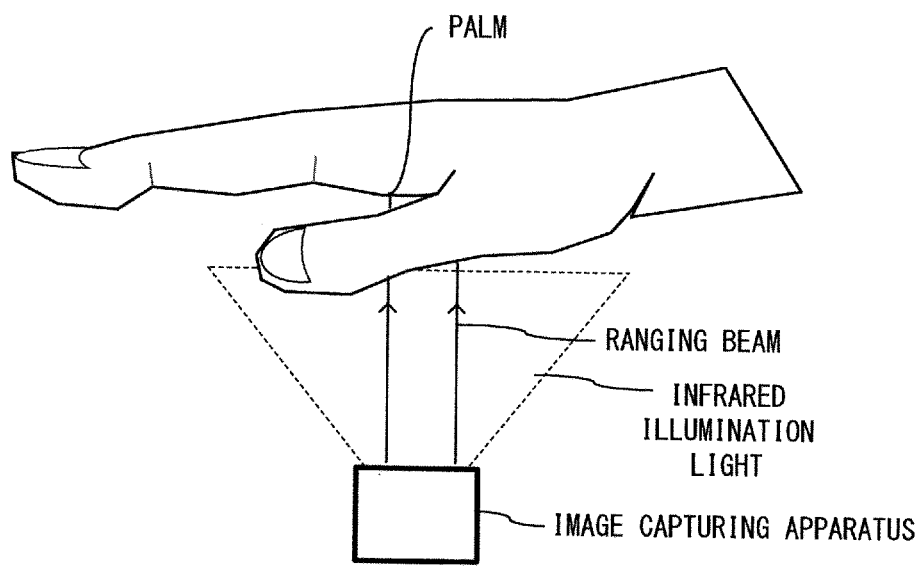
FIG. 11 illustrates how a palm is irradiated with a ranging beam emitted from a ranging LED light source of a conventional image capturing apparatus.
Figure 12:
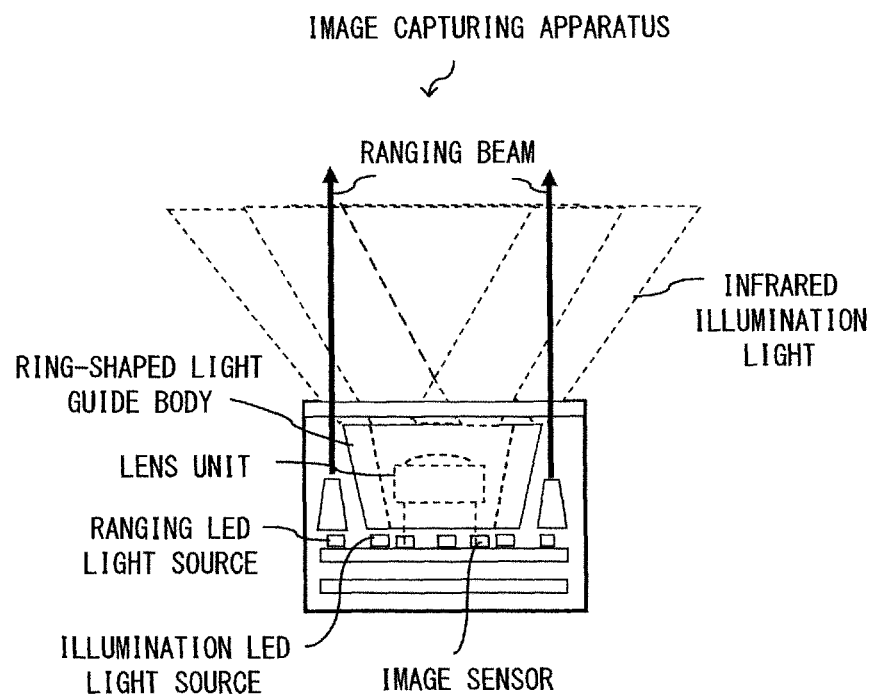
FIG. 12 illustrates an exemplary appearance of a conventional image capturing apparatus.
Figure 13:
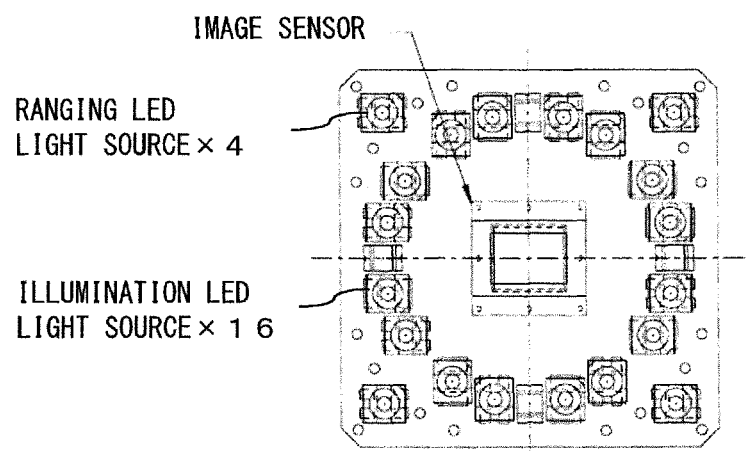
FIG. 13 is a plane view of illumination LED light sources and ranging LED light sources of a conventional image capturing apparatus.
Figure 15:
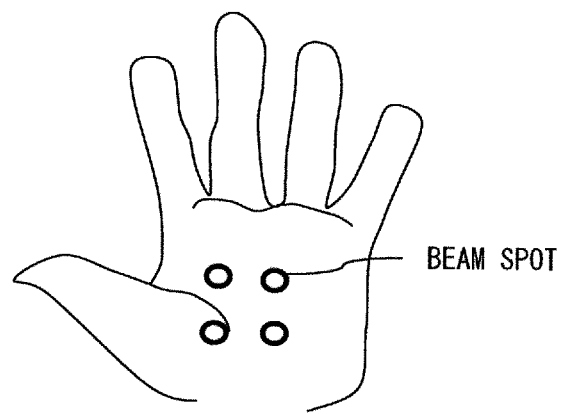
FIG. 15 illustrates beam spots provided by a conventional image capturing apparatus.
Figure 16:
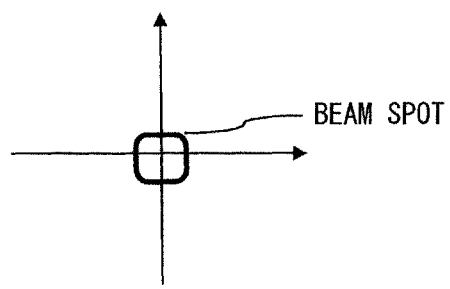
FIG. 16 illustrates the shape of a beam spot provided by a conventional image capturing apparatus.

Next, descriptions will be given of other advantageous effects of the invention by referring to FIGS. 10A and 10B. As depicted in FIG. 10B, the conventional beam generation optical system is such that when relative positions of a lens and a light source 2 are not aligned, i.e., when the center of the light source 2 and the optical axis of the lens are offset from each other, the same magnification as a beam spot is also applied to a misalignment amount (e) of the beam spot. In particular, there has been a problem that an accuracy in ranging is decreased if the configuration is made thin since a beam spot position will be excessively affected by misalignment between the light source 2 and the lens. However, the present invention provides, as indicated FIG. 10A, an optical path effectively equivalent to a path that would be achieved by a combination lens, and the optical element on the emission side serves (functions) to guide an outwardly deviating light ray that occurs at an incidence section back to the center. Hence, providing a thin configuration does not increase the influence of lens misalignment on a beam position. It is another advantageous effect of the present invention that a beam spot position is not excessively affected by misalignment.

The beam generation optical system described above (an image capturing apparatus that includes the beam generation optical system) can prevent a spot radiance from being decreased while maintaining a beam spot with a small size so that the image capturing apparatus can be thin without decreasing the sensitivity and accuracy of the ranging function. In addition, an image capturing apparatus that includes the beam generation optical system allows a ranging image of a beam spot on a palm to be accurately obtained. Hence, for example, the ranging image and an entire image of a subject such as a palm can be controlled and obtained separately from each other, thereby providing high-quality imaging data with no blurring.

EXPLANATIONS OF LETTERS OR NUMERALS 1, 21, 31, 41: Optical element
2: Light source
3, 23: Transmissive section (First transmissive section)
4, 24: Reflection section (First reflection section)
5, 25: Reflection section (Second reflection section)
6, 26: Transmissive section (Second transmissive section)
7: Optical axis
70: Housing
71: Attaching part
72: Cap
73: Printed board
80, 81, 90, 91: Member
80$a$: Upper section
82: Interface
90$a$: Convex reflective mirror
90$b$: Attachment rib
91$a$: Light incidence section
91$b$: Support part
91$c$: Concave reflective mirror

What is claimed is:

1. A beam generation optical system that causes light emitted from a light source to be incident on an optical element and causes the incident light to be reflected and emitted out of the optical element so as to generate a light beam, wherein
the optical element includes
a first transmissive section that causes the light emitted from the light source to be incident on the optical element,
a first reflection section which is located at a facing section facing the first transmissive section and from which light incident from the first transmissive section is reflected,
a second reflection section which is located around the first transmissive section and from which the light reflected from the first reflection section is reflected, and
a second transmissive section that causes the light reflected from the second reflection section to be emitted out of the optical element in an optical axis direction of the light source, wherein
the optical element includes first and second members and the optical element is formed by assembling the first and second members;
the first member including the first reflection section and the first transmissive section that are formed integrally, and
the second member including the second reflection section and the second transmissive section that are formed integrally.

2. The beam generation optical system of claim 1, wherein the first and second reflection sections each have a reflective film formed thereon.

3. The beam generation optical system of claim 1, wherein the second transmissive section forms a convex shape on an opposite side from a light-source side.

4. The beam generation optical system of claim 1, wherein the first reflection section forms a convex shape toward the light source.

5. The beam generation optical system of claim 1, wherein the second reflection section forms a convex shape on a light-source side.

6. An image capturing apparatus comprising:
a beam generation optical system that causes light emitted from a light source to be incident on an optical element and causes the incident light to be reflected and emitted out of the optical element so as to generate a light beam, wherein
the optical element includes
a first transmissive section that causes the light emitted from the light source to be incident on the optical element,
a first reflection section which is located at a facing section facing the first transmissive section and from which light incident from the first transmissive section is reflected,
a second reflection section which is located around the first transmissive section and from which the light reflected from the first reflection section is reflected, and
a second transmissive section that causes the light reflected from the second reflection section to be emitted out of the optical element in an optical axis direction of the light source, wherein
the optical element includes first and second members and the optical element is formed by assembling the first and second members,
the first member includes the first reflection section and the first transmissive section that are formed integrally, and
the second member includes the second reflection section and the second transmissive section that are formed integrally.

* * * * *